United States Patent
Ein-Gal

(10) Patent No.: US 7,666,152 B2
(45) Date of Patent: Feb. 23, 2010

(54) FOCUSING ELECTROMAGNETIC ACOUSTIC WAVE SOURCE

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 568 days.

(21) Appl. No.: 11/347,261

(22) Filed: Feb. 6, 2006

(65) Prior Publication Data

US 2007/0239081 A1    Oct. 11, 2007

(51) Int. Cl.
    *A61H 1/00*     (2006.01)
    *A61B 8/14*     (2006.01)
    *A61B 8/00*     (2006.01)

(52) U.S. Cl. ............................. 601/2; 600/459; 600/439
(58) Field of Classification Search .................. 601/1–4
    See application file for complete search history.

(56) References Cited

U.S. PATENT DOCUMENTS 3,958,559 A * 5/1976 Glenn et al. ................. 600/472
4,760,304 A * 7/1988 Oliver ........................ 310/335
5,193,527 A * 3/1993 Schafer ......................... 601/2
2003/0060738 A1 * 3/2003 Ein-gal .......................... 601/4

* cited by examiner

Primary Examiner—Long V Le
Assistant Examiner—Angela M Hoffa
(74) Attorney, Agent, or Firm—Dekel Patent Ltd; David Klein

(57) ABSTRACT

An acoustic wave device including an acoustic wave transducer adapted to generate an acoustic wave in a propagation liquid, the acoustic wave transducer having an inner contour defined by rotating a curve about a rotation axis of symmetry, wherein the curve and the acoustic wave are not parallel to the rotation axis of symmetry, and a focusing lens arranged with respect to the acoustic wave transducer so as to focus the acoustic wave emanating from the acoustic wave transducer to a focal point.

14 Claims, 1 Drawing Sheet

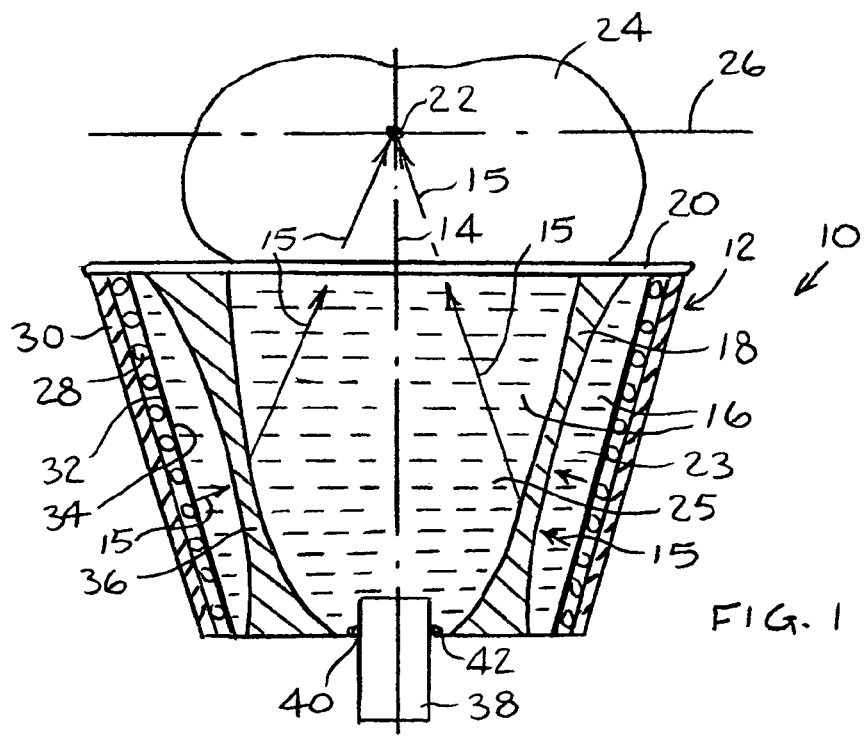
FIG. 1
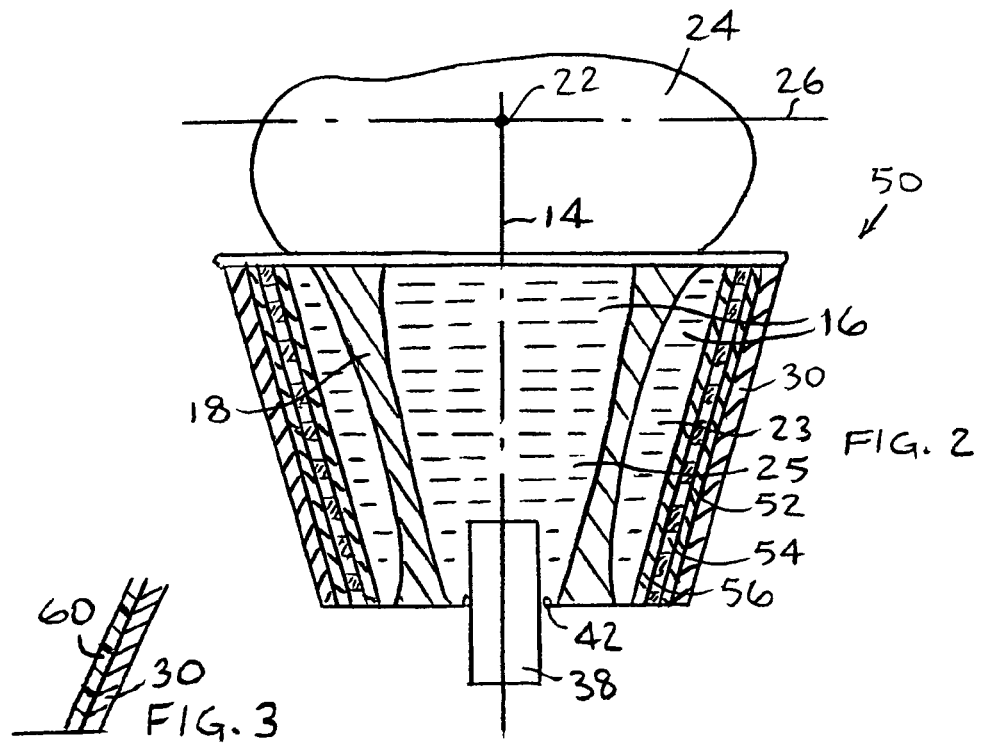
FIG. 2
FIG. 3

US 7,666,152 B2

FOCUSING ELECTROMAGNETIC ACOUSTIC WAVE SOURCE

FIELD OF THE INVENTION

The present invention relates generally to generation and focusing of acoustic waves, and specifically to generation and focusing of acoustic waves with electromagnetic energy.

BACKGROUND OF THE INVENTION

Focused acoustic waves (or shockwaves, the terms being used interchangeably throughout) are being used increasingly in medical applications. For example, acoustic waves are used for tissue ablation, diagnostic imaging, drug delivery, breaking up concretions in the body such as kidney stones, treating orthopedic diseases, combating soft tissue complaints and pain, and other therapies which employ heat, cavitation, shock waves, and other thermal and/or mechanical effects for therapeutic purposes.

The prior art typically converts electrical energy into acoustic waves, such as by generating a strong pulse of an electric or magnetic field, usually by capacitor discharge, converting the electromagnetic field into acoustic energy, and directing the energy to a target by means of an associated focusing apparatus.

Point sources for the generation of acoustic waves in a lithotripter are described in various patents, such as U.S. Pat. No. 3,942,531 to Hoff et al., and U.S. Pat. No. 4,539,989 to Forsemann et al. A planar source for generation of acoustic waves is described, for example, in U.S. Pat. No. 4,674,505 to Pauli et al.

Cylindrical sources for generation of acoustic waves are described, for example, in U.S. Pat. No. 5,058,569 to Hassler et al., and U.S. Pat. No. 5,174,280 to Gruenwald et al. Spherical sources are also mentioned in the background of U.S. Pat. No. 5,174,280.

A truncated conical acoustic wave source is described in U.S. Pat. No. 6,869,407 to Ein-Gal, the disclosure of which is incorporated herein by reference. The background section of U.S. Pat. No. 6,869,407 includes a brief description of the manner by which acoustic waves are produced by point, spherical, planar, and cylindrical sources and a description of the limitations of each of these prior art acoustic wave generation apparatuses.

SUMMARY OF THE INVENTION

It is an object of some aspects of the present invention to provide an acoustic wave generation and focusing device comprising an acoustic wave transducer and an acoustic lens that provides improved focusing capability for ultrasonic energy deposition in body tissue, and provides a more efficient and cost-effective apparatus for ultrasonic energy deposition.

Acoustic waves may be generated in a variety of ways. By way of example and not limitation, acoustic waves may be generated by an area transducer, such as a truncated conical area transducer. A coil may repel or vibrate a conical membrane to produce acoustic waves. In another example, a conducting surface electrode may be mounted on the inner contour of the conical transducer. A perforated insulator may at least partially cover the surface electrode, and may be sandwiched between the surface electrode and a return electrode. A multiplicity of electrical currents may flow through the perforations of the perforated insulator, which give rise to point sources of ultrasonic energy in the form of spherical waves emanating from the perforations.

There is thus provided in accordance with a non-limiting embodiment of the present invention an acoustic wave device an acoustic wave transducer adapted to generate an acoustic wave in a propagation liquid, said acoustic wave transducer having an inner contour defined by rotating a curve about a rotation axis of symmetry, wherein the curve and the acoustic wave are not parallel to the rotation axis of symmetry, and a focusing lens arranged with respect to said acoustic wave transducer so as to focus the acoustic wave emanating from said acoustic wave transducer to a focal point. The focusing lens may have an inner contour that defines an inner volume axisymmetric about the rotation axis of symmetry and at least partially filled with the propagation liquid, wherein an outer volume defined between an outer contour of said focusing lens and said acoustic wave transducer is at least partially filled with the propagation liquid, the inner and outer volumes being bounded by a membrane.

There is also provided in accordance with a non-limiting embodiment of the present invention, apparatus for generating highly focused acoustic waves including a non-planar axisymmetric conducting membrane and associated electromagnetic coil obtained by rotating a membrane line-segment about a rotation axis. Said rotation axis intersects the focal point to which the acoustic waves will be targeted. The conducting membrane surface is monotonous (monotonically increasing in the symmetry axis for increasing radial distance from the symmetry axis) and the distance from any membrane point to a plane perpendicular to the rotation axis and intersecting the focal point is inversely proportional to the distance of said membrane point to the rotation axis. An axisymmetric acoustic lens surface associated with said membrane is obtained by rotating a lens cross-section segment about said rotation axis. Said lens cross-section-segment is determined by the relative propagation speeds in the acoustic lens material and the propagating liquid subject to the requirement that the waves produced by the vibrating membrane are focused by the lens onto the focal region.

In some embodiments of the present invention, the focal point is located closer to the larger cone base of a truncated conical membrane surface. Said surface is produced by rotating a linear membrane line-segment about a rotation axis wherein said membrane line-segment and said rotation axis are on the same plane and are not orthogonal so as not to form a planar membrane. A lens associated with said conical membrane surface is formed by rotating a generally concave circular lens cross-section-segment about said rotation axis. Said lens cross-section-segment is generally concave since the propagation speed of the lens is faster than that of the propagating liquid.

In other embodiments of the present invention, a non-conical membrane surface may be obtained by rotating a substantially circular membrane line segment about a rotation axis. The acoustic lens associated with said non-conical membrane surface is obtained by rotation of a lens circular cross-section about the said rotation axis.

There is also provided in accordance with an embodiment of the present invention, an acoustic wave device including an electrical element disposable on an inner contour of a support of an acoustic wave transducer, the inner contour having a non-cylindrical and non-flat shape, the electrical element being a really configured on the inner contour for radiating acoustic waves inwardly from the inner contour.

Further, in accordance with an embodiment of this invention, the electrical element includes a coil mountable on an inner contour of a support of an acoustic wave transducer and a membrane shaped to conform to the inner contour, wherein the coil is adapted to move the membrane inwards from the support.

Further in accordance with an embodiment of this invention the electrical element includes a coil mountable on an inner contour of a support of an acoustic wave transducer and a magnet disposable on the support adapted to generate a magnetic field that repels the coil inwards from the support.

Still further in accordance with an embodiment of this invention the electrical element includes a conducting surface electrode mountable on the inner contour, a perforated insulator that at least partially covers the conducting surface electrode, and a return electrode disposed on a side of the perforated insulator opposite to the conducting surface electrode.

There is also provided in accordance with an embodiment of the invention an acoustic wave device including an electrical element disposable on an inner contour of a support of an acoustic wave transducer, the electrical element being areally configured on the inner contour for radiating acoustic waves inwardly from the inner contour, and a magnet disposable on the support adapted to generate a magnetic field that repels the electrical element inwards from the support. The electrical element may be a coil, for example. The support may be non-cylindrical and non-flat.

There is also provided in accordance with an embodiment of this invention an acoustic wave device including an electrical element disposable on an inner contour of a support of an acoustic wave transducer, the electrical element being areally configured on the inner contour for radiating acoustic waves inwardly from the inner contour, and a perforated insulator that at least partially covers the electrical element. The support may be non-cylindrical and non-flat.

In accordance with an embodiment of the invention the electrical element includes a conducting surface electrode mountable on the inner contour, and a return electrode disposed on a side of the perforated insulator opposite to the conducting surface electrode.

BRIEF DESCRIPTION OF THE DRAWINGS

FIG. 1 is a simplified partially sectional illustration of an acoustic wave device, constructed and operative in accordance with an embodiment of the invention;

FIG. 2 is a simplified partially sectional illustration of an acoustic wave device, constructed and operative in accordance with another embodiment of the invention; and FIG. 3 is a simplified partially sectional illustration of an acoustic wave device similar to that of FIGS. 1 and 2, but with a piezoelectric or magnetostrictive transducer as the producer of shockwaves, constructed and operative in accordance with another embodiment of the invention.

DETAILED DESCRIPTION OF EMBODIMENTS

Reference is now made to FIG. 1, which illustrates an acoustic wave device 10 constructed and operative in accordance with an embodiment of the present invention.

In the illustrated embodiment, acoustic wave device 10 includes an acoustic wave transducer 12, which may be shaped like a truncated cone with an axis of symmetry (rotation axis of symmetry) 14. The inner volume of acoustic wave generation device 10 may be filled with a propagation fluid 16. A focusing lens 18 may be arranged with respect to transducer 12 so as to focus an acoustic wave emanating from transducer 12 to a focal point 22, which may lie on the axis of symmetry 14. Lens 18 is adapted to comply with the condition that the waves generated by the transducer are focused upon focal point 22. Such adaptation is a function of the relative wave propagation speeds in the material of lens 18 and propagation fluid 16.

The cone shaped acoustic wave generation device 10 shown in this FIG. 1 is by way of illustration and not limitation and it is noted that the present invention is not limited to a cone-shaped device and may be carried out with other shapes as well.

The end face of acoustic wave device 10 in the direction of focal point 22 may be covered with a membrane 20. Acoustic wave device 10 may be placed against or near a target 24 which it is desired to treat. Acoustic waves 15 generated by transducer 12 may propagate towards focal point 22 located in target 24 via focusing lens 18, propagating fluid 16, and through membrane 20. Acoustic wave transducer 12 has an inner contour defined by rotating a curve (e.g., the slanted line on the contour of the cone) about rotation axis of symmetry 14, wherein the curve and the acoustic wave 15 are not parallel to the rotation axis of symmetry 14.

Acoustic waves may be generated in a variety of ways. In the non-limiting embodiment of FIG. 1, transducer 12 is an area transducer, such as a truncated conical area transducer. The area transducer comprises an electrical element 28, such as a coil or a plurality of short coil segments electrically connected in parallel, mounted on an inner surface of a truncated conical support 30. A conducting membrane 32 is shaped to conform to the inner contour of conical support 30 and is disposed on electrical element 28. Electrical element 28 is adapted to move (e.g., repel or vibrate) membrane 32 inwards from conical support 30. Acoustic waves thus generated will propagate in a direction inwards from the contour of transducer 12 into a portion of propagation liquid 16 disposed between membrane 32 and focusing lens 18. The waves generated in this manner will pass through lens 18 and be focused towards focal point 22 within target 24.

It is noted that prior art focusing lenses are basically perpendicular to the axis of symmetry. In contrast, in the present invention, the focusing lens 18 at least partially (or fully) circumscribes the rotation axis 14 and has an inner contour defines an inner volume 25, which is axisymmetric about axis 14 and at least partially filled with propagation liquid 16. An outer volume 23 defined by the space between the outer contour of the focusing lens 18 and the vibrating transducer element (i.e., membrane 32) is at least partially filled with propagation liquid 16.

In mathematical terms, membrane 32 may comprise a non-planar axisymmetric conducting membrane (axisymmetric about axis of symmetry 14) obtained by rotating a membrane line-segment 34 about a rotation axis (axis 14) that intersects the focal point 22 to which the acoustic waves will be targeted. The conducting membrane surface is monotonous (monotonically increasing in the direction of axis 14 as one goes out further radially from axis 14). The distance from any membrane point to a plane 26 perpendicular to the rotation axis (axis 14) and intersecting the focal point 22 is inversely proportional to the distance of that membrane point to the rotation axis (axis 14).

Lens 18 may comprise an axisymmetric acoustic lens surface obtained by rotating a lens cross-section segment 36 about the rotation axis (axis 14). The lens cross-section-segment 36 is determined by the relative propagation speeds in the acoustic lens material and the propagating liquid subject to the requirement that the waves produced by the vibrating membrane are focused by the lens onto the focal region. The lens cross-section segment 36 is generally concave facing axis 14 since the propagation speed of the lens 18 is faster than that of the propagating liquid 16. For example, the shape of the lens 18 (and the lens cross-section-segment 36) that faces axis 14 may be concave and the opposite face may be straight or concave facing the inner surface of conical support 30.

An imaging device 38, such as but not limited to, an x-ray probe or ultrasonic probe, may be disposed in a bore 40 along axis of symmetry 14 for viewing the focal point 22 in target 24. An O-ring 42 or other suitable seal may be used to seal imaging device 38 with respect to the inner volume 25.

Reference is now made to FIG. 2, which illustrates an acoustic wave device 50 constructed and operative in accordance with an embodiment of the present invention. Acoustic wave device 50 is similar in construction to acoustic wave device 10, with like elements being designated by like numerals. Acoustic wave device 50 differs from acoustic wave device 10 in the way the acoustic waves are generated. In the non-limiting illustrated embodiment, a conducting surface electrode 52 may be mounted on the inner contour of the conical support 30. A perforated insulator 54 may at least partially cover the surface electrode 52, and may be sandwiched between the surface electrode 52 and a return electrode 56. A multiplicity of electrical currents may flow through the perforations of the perforated insulator 54, which give rise to point sources of ultrasonic energy in the form of spherical waves emanating from the perforations. Focusing lens 18 may focus the wave energy to focal point 22 as described hereinabove.

Reference is now made to FIG. 3. Instead of the area transducer with coils shown in FIG. 1 and instead of the electrodes of FIG. 2, a different transducer may be used to produce the shockwaves. For example, a plurality of piezoelectric or magnetostrictive transducers 60 may be mounted on a support (e.g., the conical support 30) and produce waves that may be focused by an acoustic lens, such as lens 18 described hereinabove. Piezoelectric transducers for generating shockwaves are commercially available from many manufacturers, such as Physik Instrumente (PI) GmbH of Karlsruhe/Palmbach, Germany. Magnetostrictive transducers may be constructed of smart materials such as Terfenol-D, commercially available, for example, from Etrema Products, Inc., Ames, Iowa. Terfenol-D stands for terbium (TER), iron (FE), Naval Ordnance Labs (NOL), and Dysprosium (-D) and has the largest room temperature magnetostriction of any known material. It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An acoustic wave device comprising:
   an acoustic wave transducer adapted to generate an acoustic wave in a propagation liquid, said acoustic wave transducer having an inner contour defined by rotating a curve about a rotation axis of symmetry, wherein the curve and the acoustic wave are not parallel to the rotation axis of symmetry; and
   a focusing lens arranged with respect to said acoustic wave transducer so as to focus the acoustic wave emanating from said acoustic wave transducer to a focal point, wherein said focusing lens at least partially circumscribes said rotation axis of symmetry and has an inner contour that defines an inner volume, which is axisymmetric about said rotation axis of symmetry and is at least partially filled with said propagation liquid, and has an outer volume defined by a space between an outer contour of said focusing lens and said acoustic wave transducer and which is at least partially filled with said propagation liquid, wherein said inner contour of said focusing lens is radially inwards towards said rotation axis of symmetry relative to said outer contour.

2. The acoustic wave device according to claim 1, wherein the inner and outer volumes being bounded by a membrane.

3. The acoustic wave device according to claim 1, wherein said focal point lies on the rotation axis of symmetry.

4. The acoustic wave device according to claim 1, wherein said acoustic wave transducer is shaped as a truncated cone.

5. The acoustic wave device according to claim 1, wherein said acoustic wave transducer comprises an electrical element mounted on an inner surface of a conical support, and a conducting membrane shaped to conform to the inner surface of said conical support and disposed on said electrical element, said electrical element being adapted to move said membrane inwards from said conical support so as to generate acoustic waves that propagate in a direction inwards from said conical support into a portion of the propagation liquid disposed between said membrane and said focusing lens, said waves passing through said focusing lens and being focused towards said focal point.

6. The acoustic wave device according to claim 5, wherein said electrical element comprises an electrical coil.

7. The acoustic wave device according to claim 5, wherein said electrical element comprises a plurality of coil segments electrically connected in parallel.

8. The acoustic wave device according to claim 1, wherein said focusing lens is concave facing said axis of symmetry.

9. The acoustic wave device according to claim 1, wherein said acoustic wave transducer comprises a conducting surface electrode mounted on an inner contour of a conical transducer, and wherein a perforated insulator at least partially covers said surface electrode and is sandwiched between said surface electrode and a return electrode, wherein a multiplicity of electrical currents flow through perforations of said perforated insulator.

10. The acoustic wave device according to claim 1, wherein said acoustic wave transducer comprises a piezoelectric transducer.

11. The acoustic wave device according to claim 1, wherein said acoustic wave transducer comprises a magnetostrictive transducer.

12. The acoustic wave device according to claim 1, wherein the curve and the acoustic wave are not perpendicular to the rotation axis of symmetry.

13. The acoustic wave device according to claim 1, further comprising an imaging device disposed in a bore along said rotation axis of symmetry for viewing the focal point.

14. The acoustic wave device according to claim 13, further comprising a seal that seals said imaging device with respect to the inner volume.

* * * * *